United States Patent [19]

Caro

[11] Patent Number: 4,608,180

[45] Date of Patent: Aug. 26, 1986

[54] SEPARATION PROCESS

[75] Inventor: Colin G. Caro, Putney, England

[73] Assignee: The British Petroleum Company p.l.c., London, England

[21] Appl. No.: 745,827

[22] Filed: Jun. 18, 1985

Related U.S. Application Data

[63] Continuation of Ser. No. 575,764, Feb. 1, 1984, abandoned.

[30] Foreign Application Priority Data

Feb. 3, 1983 [GB] United Kingdom ............. 8302949

[51] Int. Cl.⁴ ............................................. B01D 33/00
[52] U.S. Cl. ................................. 210/780; 210/791; 210/799; 210/356
[58] Field of Search .............. 210/356, 780, 781, 791, 210/798, 799

[56] References Cited

U.S. PATENT DOCUMENTS

| | | | |
|---|---|---|---|
| 2,027,681 | 1/1936 | Durant et al. | 210/356 |
| 2,837,032 | 6/1958 | Horsting | 210/356 X |
| 3,633,753 | 1/1972 | Petitjean | 210/356 |
| 3,747,769 | 7/1973 | Brumfield | 210/350 |
| 3,894,950 | 7/1975 | Ayres et al. | 210/356 X |
| 3,947,362 | 3/1976 | Etani | 210/416 |
| 4,058,465 | 11/1977 | McKee | 210/386 |
| 4,090,965 | 5/1978 | Fuchs | 210/356 |
| 4,302,310 | 11/1981 | Watson et al. | 204/186 |
| 4,303,533 | 12/1981 | Fremont | 210/791 |

FOREIGN PATENT DOCUMENTS

| | | |
|---|---|---|
| 403849 | 1/1934 | United Kingdom . |
| 422748 | 1/1935 | United Kingdom . |
| 1418806 | 12/1975 | United Kingdom . |

*Primary Examiner*—John Adee
*Attorney, Agent, or Firm*—Morgan, Finnegan, Pine, Foley & Lee

[57] ABSTRACT

A process for separating suspended material from a fluid comprising flowing the fluid through a porous matrix. The porous matrix is elastically deformable and restrained at its outlet end. The flow rate is sufficiently large so as to produce non uniform deformation of the porous matrix and thereby a gradient of porosity in the direction of fluid flow. At least a part of the suspended material is separated by retention within the porous matrix. The porous matrix/fluid system has a self cleaning capability.

17 Claims, 12 Drawing Figures

FIG.12 Matrix Height and Pressure Drop vs. Time for water flow (with suspended solids) through DK50.

SEPARATION PROCESS

This application is a continuation, of application Ser. No. 575,764, filed Feb. 1, 1984, now abandoned.

This invention relates to processes involving the flow of a fluid through a deformable porous matrix, particularly to processes involving the flow of heterogeneous fluids through a porous matrix to separate one of the phases or a component of a phase.

Processes involving the flow of fluids having a continuous phase and a discontinuous phase through a porous matrix to separate the phases are well known (e.g. filtration). The channel dimensions of the porous matrix are usually fixed throughout the matrix and are normally chosen in relation to the size of the particles of the discontinuous phase, so that the particles collect on the upstream surface of the matrix, to be removed, for example by backwashing or changing the matrix.

The present invention uses an elastically deformable porous matrix and is based on the finding that such matrices can be made to undergo non-uniform deformation when subjected to fluid flow through them.

According to the present invention, there is provided a process for separating suspended material from a fluid comprising flowing the fluid through a porous matrix, the porous matrix being elastically deformable and restrained, and the fluid flow rate being sufficiently large so as to produce substantial non-uniform deformation and thereby a gradient of porosity in the direction of fluid flow, whereby at least a part of the suspended material is separated by retention within the porous matrix.

Filtration or separation of suspended material from liquids by passing the liquid through a porous matrix such as polyurethane foam is known. Separation by use of a fluid flow rate sufficient to cause substantial non-uniform deformation of the porous matrix offers certain advantages over the prior art process. The flow rate required to induce non-uniform deformation of the porous matrix depends on the matrix being used but is usually significantly greater than those used for conventional filtration processes. Typically for fluids having a viscosity of 5 cp or less at the temperature of the separation process, the fluid flow rate through the porous matrix is 90 m$^3$m$^{-2}$hr$^{-1}$ or more and the deformation of the porous matrix is 10% or more.

The porous matrix may be restrained by means of a substantially non-deformable member on either or both the outlet or inlet sides of the matrix. The member may be a mesh of e.g. metal, plastic or cloth with perforations larger than the channel dimensions of the undeformed matrix.

If the restraint is on the outlet side of the porous matrix, flow of fluid through the matrix will induce non-uniform compaction which increases from the inlet side to the outlet side. It is envisaged that if the restraint is on the inlet side, fluid flow will tend to induce non-uniform deformation.

If the channel dimensions are uniform through the undeformed porous matrix, it follows that during the fluid flow, there will be a variation in the channel dimensions throughout the porous matrix from the inlet to the outlet side.

It is believed that the deformation is, at least in part, drag-induced deformation resulting from the fluid flow. Variation in the rate of fluid flow will, therefore, vary the extent of the deformation. The drag-induced deformation is cumulative in the direction of flow and it follows that the non-uniformity of deformation will also vary with varying flow rate. Also the process is dependent on the properties of the porous matrix including the pore size.

The fact that deformation is non-uniform in the direction of fluid flow and, hence, that there is a non-uniformity of the channel dimensions through the porous matrix can be used to increase the efficiency, flexibility and versatility of separation processes. Uses will be illustrated with reference to the preferred embodiment, of non-uniform compaction of the porous matrix with a corresponding non-uniform decrease in channel dimensions from the inlet to the outlet side of the matrix.

In a separation process, therefore, where the shape and volume of the particles forming the discontinuous phase are such that they can enter the channels of the undeformed matrix but not the deformed channels deeper in the matrix, then the particles will collect in the channels of the matrix through which they have been able to migrate.

Ideally if the particles retained a discrete identity within the matrix it would be expected that reduction in the fluid flow rate would allow return of the matrix to its undeformed state and would allow release of the particles into the fluid flow. However it appears that the accumulation of particles can oppose the release phenomena. It has been found that rapid variation of the fluid flow rate e.g. between zero and operational flow rate has the effect of facilitating the release of the particles so that they may be flushed out in the direction of fluid flow. The need for backwashing of the matrix to release the particles may thus be eliminated. The fraction of the particles released appears to be dependent on the pore size of the matrix and the particle size.

Backwashing may be used if desired, however, and the present invention should improve the efficiency of backwashing. The application of some back flow may also increase the rate and extent of recovery of the matrix.

Alternatively, the separated particles within the matrix may be removed from the matrix by standard procedures such as distillation, extraction, heating, evacuation or dissection.

With a heterogeneous fluid the continuous phase may be a gas or a liquid and the discontinuous phase may be a fluid or a solid. The principle can thus be applied to a very wide range of separations including gas-liquid, gas-solid, liquid-liquid, and liquid-solid separations. It could also have utility in three phase systems, such as gas-liquid-solid systems. The term "particle" when used with reference to the discontinuous phase will be understood to include either solid or liquid particles, or both.

Preferably the variable used to control the extent of deformation and hence the extent of variation in channel dimensions is the rate of fluid flow through the matrix which, in its turn, is related to the pressure difference across the matrix. However, the extent of deformation could be altered in other ways, e.g. by changing the dimensions of the matrix.

The other main variables influencing the extent of deformation will be the physical properties of the matrix and the viscosity of the fluid. Thus the physical properties of a porous matrix could be varied by, for example, (a) the use of open cell foams of different polymeric materials e.g. polyvinyl chloride, polyurethane or rubber with different mechanical properties or different porosities, or (b) by including mechanical devices, e.g. springs, in the matrix or by (c) using a combination of materials having differing elastic properties or, for example, by otherwise loading or tensioning the matrix. The loading or tensioning of the spring in case (b) may be altered externally.

Also the deliberate addition of chosen particles to a matrix may be used effectively to alter its pore size and hence its degree of deformation in response to flow. Thus the retention characteristics of the matrix may be altered. In this way, greater flexibility may be achieved in producing desired filtration properties than by use of the matrix alone. The added particles may interact specifically with the particles being filtered out and thereby selectively remove additional material from a fluid stream, the material associated with the particles then being recovered from the matrix by some suitable technique.

The viscosity of the fluid may be varied by changing the fluid at an appropriate time or, with the same fluid, by varying the conditions of operation, e.g. altering the temperature or adding to the fluid, another miscible fluid of different viscosity. Further it is envisaged that the flow properties of the fluid through the porous matrix may be modified by the use of materials such as drag reducing polymers or surfactants.

The fluid, porous matrix and operating conditions should be chosen to provide an extent of deformation and change in channel dimensions appropriate to the separation required and experiments may be necessary to determine the optimum conditions.

The porous matrix capable of exhibiting non-uniform deformation may be a polymer foam or other coherent material with interconnecting pores providing channels through which flow can occur. However, the matrix may also be made up of discrete elastically deformable particles, there being a change in the amount of void space between the particles as a result of fluid flow. The channels may be of macro to micro dimensions.

The matrix may have varying physical properties throughout its depth, e.g. by using layers of different materials or by using a latex foam with different degrees of vulcanisation throughout it.

The porous matrix may be comprised of a fibrous material or it is envisaged that it may be a molecular array e.g. a gel.

Suitable porous matrices exhibiting non-uniform deformation under certain conditions of fluid flow rate include elastomeric foamed plastics materials such as certain polyurethane foams and natural and synthetic rubber foams and include discrete elastically deformable particles of natural rubber based material in granular form. Also envisaged as suitable for the separation process are certain elastically deformable felts.

The fluids are preferably liquids particularly liquid-solid combinations. They may be, for example, aqueous, organic, or inorganic and have a wide range of fluid properties, such as viscosity, which might vary from below that of water to above that of a heavy petroleum fraction (e.g. lubricating oil). The preferred fluid is water based. Also gas/solid systems are envisaged e.g. aerosols.

The matrix may be disposed in any suitable configuration to give straight-through linear flow, radial flow, inwards or outwards, or any other flow pattern. An example of radial flow would be a porous matrix in the form of a hollow cylinder, the fluid flow being from the inside of the cylinder to the outside or vice-versa.

With some configurations the restraint may be provided by the matrix itself, e.g. with an annular matrix the hoop stress can be employed to restrain the outlet side from movement in the direction of flow.

Preferably the configuration is chosen so as to minimise restraint of the porous matrix other than in the direction of flow, e.g. by keeping side wall surface area to a minimum and/or keeping friction between side walls and the porous matrix to a minimum.

It will be apparent that the invention can be utilised in a variety of ways and have numerous potential applications.

Thus a single porous matrix could be used to fractionate a discontinuous phase having a range of particle sizes, the particles being retained at different levels of the matrix. Alternatively, a single porous matrix could be used to separate different particle sizes in succession, the fluid being recycled and the channel dimensions varied for each cycle. As the pore size in an undeformed porous matrix is usually not uniform i.e. the size varies around the nominal pore size, separation according to particle size occurs during fluid flow but there may be a spread of sizes. In a preferred configuration the average particle size retained in the matrix shows a decrease in the direction of fluid flow.

A series of matrices of differing channel dimensions could also be used to separate differently sized particles, the difference in channel dimensions being achieved by varying the physical properties of the matrices or by having different flow rates across the same basic type of matrix.

Among the separations that could be effected using the present invention are:

Separation of aerosol particles from gases, e.g. separating combustion solids from flue gases Separation of solid particles from liquids, e.g. purification of industrial effluents for re-use or safe disposal Separation of liquid particles from liquids, e.g. coalescence and separation of oil-in-water or water-in-oil emulsions Separation of a component from a continuous phase where the discontinuous phase sorbs it selectively.

The discontinuous phase may be separated from the continuous phase by means of the present invention, and the selectively-sorbed component removed by standard procedures (e.g. by distillation, extraction, heating or evacuation).

Where the pressure difference across the matrix is maintained by pumping, a pump failure will cause the matrix to recover and may allow retained particles to escape. Some alarm system and safety mechanism may be advisable, therefore. For example, a sensor measuring the pressure drop across the matrix could signal a divert valve downstream of the matrix to operate if the pressure drop falls below a predetermined value, thereby preventing retained particles escaping into the continuous phase outlet from the separation unit. Alternatively, a sensor or monitor of say, the pressure drop across the matrix could be programmed to cause periodic emptying of the matrix in, say, a filtration application.

Although the essential feature of the present invention is control of the deformation of the matrix by control of the operating conditions, the deformation may be supplemented or modified by external forces, e.g. by pre-stressing or by using the matrix as part of a centrifugal filter.

The invention will now be described by way of example only and with reference to FIGS. 1 to 12 of the accompanying drawings.

Table 1 shows the characteristics of the porous matrices.

TABLE 1

| Matrix | Smallest Pore (μm) | Average Pore Size Range | Largest Pore (μm) | Density Kg/m$^{-3}$ | Hardness (Kg) | Hardness Grade | Fatigue Class |
|---|---|---|---|---|---|---|---|
| DK2 | ~150 | 380–700 | ~1000 | 14 | | | |
| DK15 | ~100 | 200–400 | ~750 | 30 | | | |
| DK50 | ~70 | 130–250 | ~450 | 50 | | | |
| D36 | ~120 | 300–600 | ~1000 | 18 | 9.5+10.5 | 50 | A |
| D7 | | 300–600 | | 22 | 19–23 | 130 | A |
| D39 | ~120 | 200–500 | | 31.5 | 170–195 | 170 | S |
| AB 26B | ~150 | 700–1000 | ~1000 | 20 | | | |
| GC 356 | ~100 | 400–700 | ~1000 | 33 | | | |
| GC 364 | ~100 | 400–700 | ~1000 | 40 | | | |
| S2 | | 25–100 | | 120 | | | |
| S6 | | | | 160 | | | |
| S7 | | | | 160 | | | |
| S8 | | 75–100 | | 80 | | | |
| C | | particle size (100% less than 4 mm. 60% less than 2 mm) | | 450–930 (packed state) | (free state - closely packed state) | | |

DK2, DK15, DK50 - hot cure open cell polyurethane (polyether based) foam (BP Chemicals)
D36, D7, D39 - standard grade open cell polyurethane (polyether based) foam (Dunlop)
S2, S6, S7, S8 - moulded latex foam (Malaysian Rubber Producers Research Association)
C - Crusoe powdered natural rubber (Harrisons and Crosfield)
AB26B, GC356, GC364 - High resilience open cell polyurethane (polyether based) foam (BP Chemicals).
Pore sizes were determined by electron microscopy.
(S2, S8 have small pores set within larger cavities ~300–500 μm).

Figure 1:
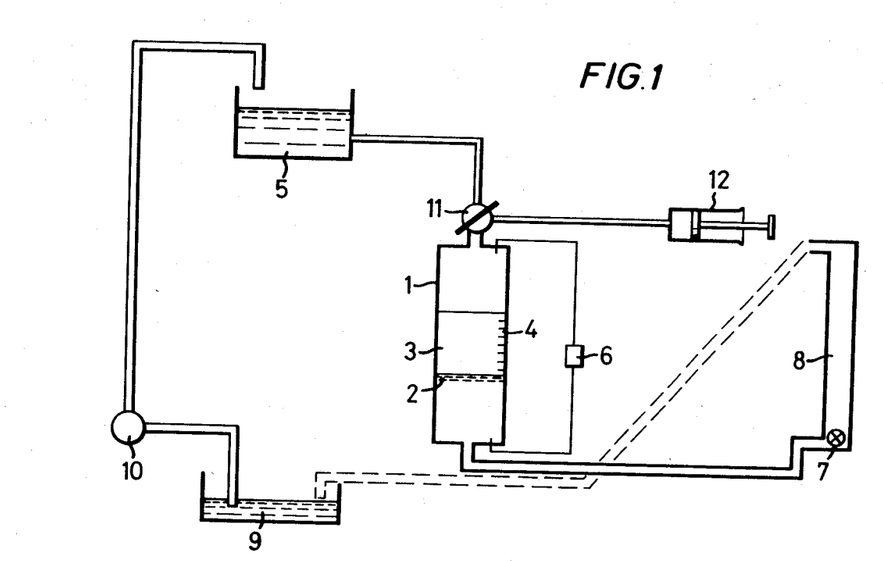
FIG. 1 shows a schematic diagram of the apparatus used for observing the flow of fluids and particles through a porous matrix.

A transparent cylinder or flow tube 1 was arranged vertically and fitted with a wire mesh grid support 2 near its lower end. The porous matrix 3 to be observed, in this case an open cell polyurethane foam, was fabricated to closely fit within the cylinder 1 and was supported by the grid 2. A number of transverse reference lines 4 were marked on the undeformed foam before its insertion into the cylinder 1.

A water tank 5 was used as the source of fluid flow and was capable of passing water through the foam under gravity at different flow rates. The pressure difference across the foam was measured by a differential pressure transducer 6 connected to an electrical recorder (not shown). The flow rate of water through the foam 3 was regulated by valve 7 and measured by a flow measuring tube 8 of the rotameter type. The water emerging from the flow measuring tube 1 was collected in a reservoir 9 and recycled by a pump 10 to the water tank 5. A similar apparatus was used for experiments using glucose syrup as the fluid. When the fluid was air it was drawn through the apparatus by means of a pump.

A three-way valve 11 at the inlet to the flow tube 1 was used to enable introduction of solid particles to the liquid flow. The solid particles in the liquid were contained in a syringe-like vessel 12. Operation of the plunger of vessel 12 and use of the three way valve 11 allowed the solid particles to be introduced into the liquid flow. Alternatively the solid particles were introduced directly by suspending them in water tank 5. Sample points were located immediately upstream and downstream of the flow tube 1 to enable the filtration efficiency of the matrix 3 to be determined.

The following experiments were carried out to illustrate the deformation of the porous matrix by fluid flow. Open cell polyurethane foam (Dunlop Limited) was used as the deformable porous matrix. Two grades of foam (D7 and D36) were used both with undeformed pore sizes ranging approximately from 300–600 μm but with different physical properties.

The matrices were in the form of cylinders 5 cm in diameter and approximately 7 cm in length. Graduation marks were made along their length to enable measurement of deformation. The foam cylinders were inserted into cylindrical perspex containers in which they were supported on wire mesh grids.

Figure 2:
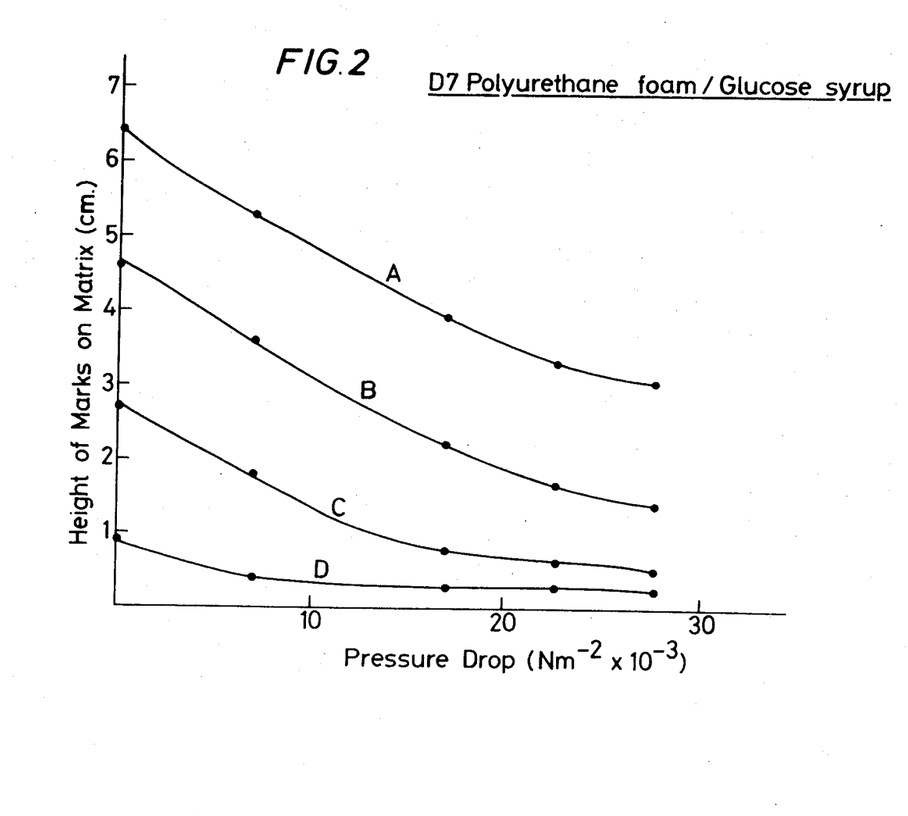
FIGS. 2 and 3 show graphs of the deformation of D7 and D36 polyurethane foams against fluid pressure drop for glucose syrup and water respectively.
Figure 3:
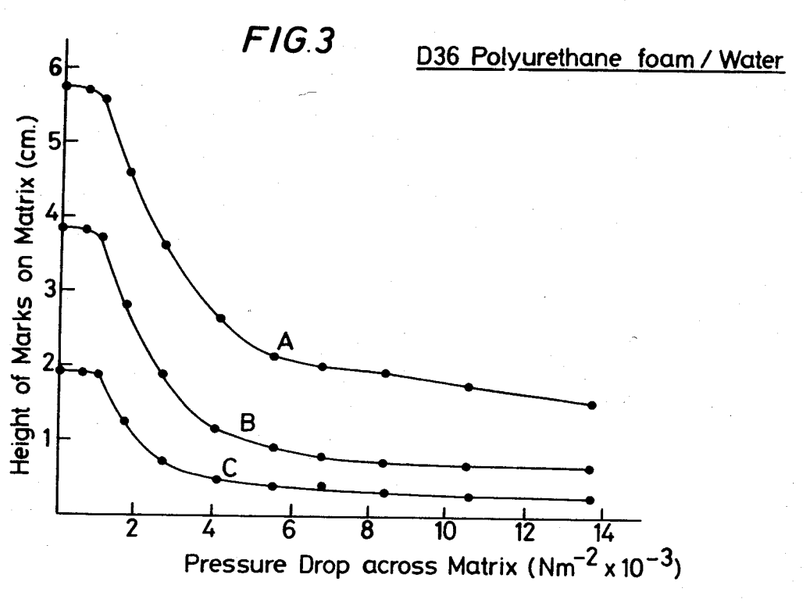

Liquid was passed vertically downwards through the foam matrix at different flow rates. After the matrix had compressed to a steady-state configuration, its deformation and the pressure drop across it were measured. With polyurethane D7 the liquid was glucose syrup (viscosity at 15° C.=17,500 cP) while with polyurethane D36 the liquid was water at 20° C. (about 1 cP). The results of Table 2 and Table 3 are shown graphically on FIGS. 2 and 3.

TABLE 2

(a) Polyurethane D7

| | | Pressure drop across foam ($Nm^{-2} \times 10^{-3}$) | | | | |
|---|---|---|---|---|---|---|
| | | 0 | 7.1 | 17.1 | 22.7 | 27.6 |
| Height of marks above rigid grid (cm) | A | 6.4 | 5.3 | 3.9 | 3.3 | 3.0 |
| | B | 4.6 | 3.6 | 2.2 | 1.65 | 1.35 |
| | C | 2.7 | 1.8 | 0.75 | 0.6 | 0.5 |
| | D | 0.9 | 0.4 | 0.25 | 0.25 | 0.2 |
| Separation between marks (cm) | A-B | 1.8 | 1.7 | 1.7 | 1.65 | 1.65 |
| | B-C | 1.9 | 1.9 | 1.45 | 0.95 | 0.85 |
| | C-D | 1.8 | 1.4 | 0.5 | 0.45 | 0.3 |

TABLE 3

(b) Polyurethane D36

| | | Pressure drop across foam ($Nm^{-2} \times 10^{-3}$) | | | | | |
|---|---|---|---|---|---|---|---|
| | | 0 | 1.7 | 4.0 | 6.7 | 10.6 | 13.7 |
| Height of marks above grid (cm) | A | 5.7 | 4.6 | 2.65 | 2.0 | 1.8 | 1.55 |
| | B | 3.8 | 2.8 | 1.15 | 0.8 | 0.7 | 0.7 |
| | C | 1.9 | 1.25 | 0.45 | 0.4 | 0.3 | 0.3 |
| Separation between marks (cm) | A-B | 1.9 | 1.8 | 1.5 | 1.2 | 1.1 | 0.85 |
| | B-C | 1.9 | 1.55 | 0.7 | 0.4 | 0.4 | 0.4 |
| | C-Base | 1.9 | 1.25 | 0.45 | 0.4 | 0.3 | 0.3 |

Figure 4:
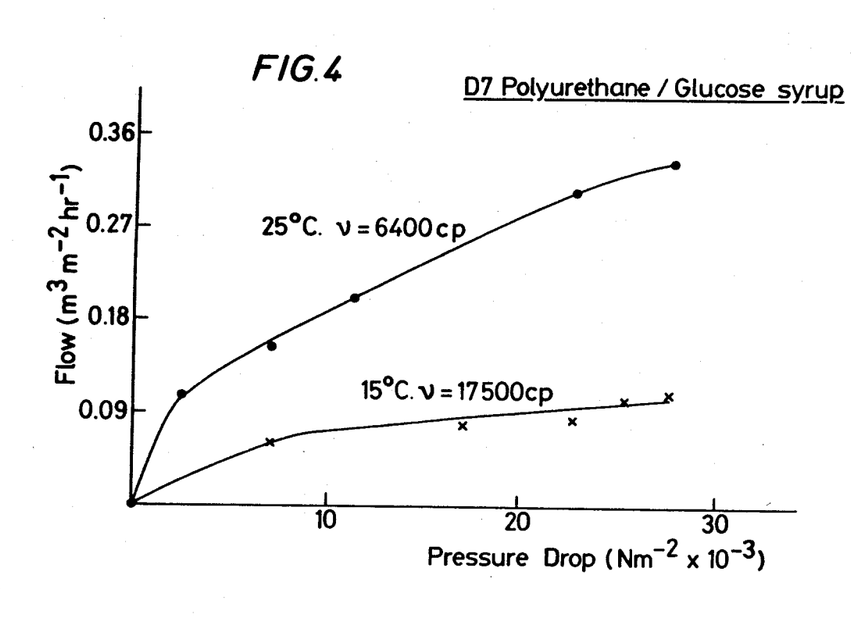
FIGS. 4 and 5 shows graphs of the variation of flow rate and pressure drop of glucose syrup and water respectively across D7 and D36 polyurethane foams at a steady state matrix deformation.
Figure 5:
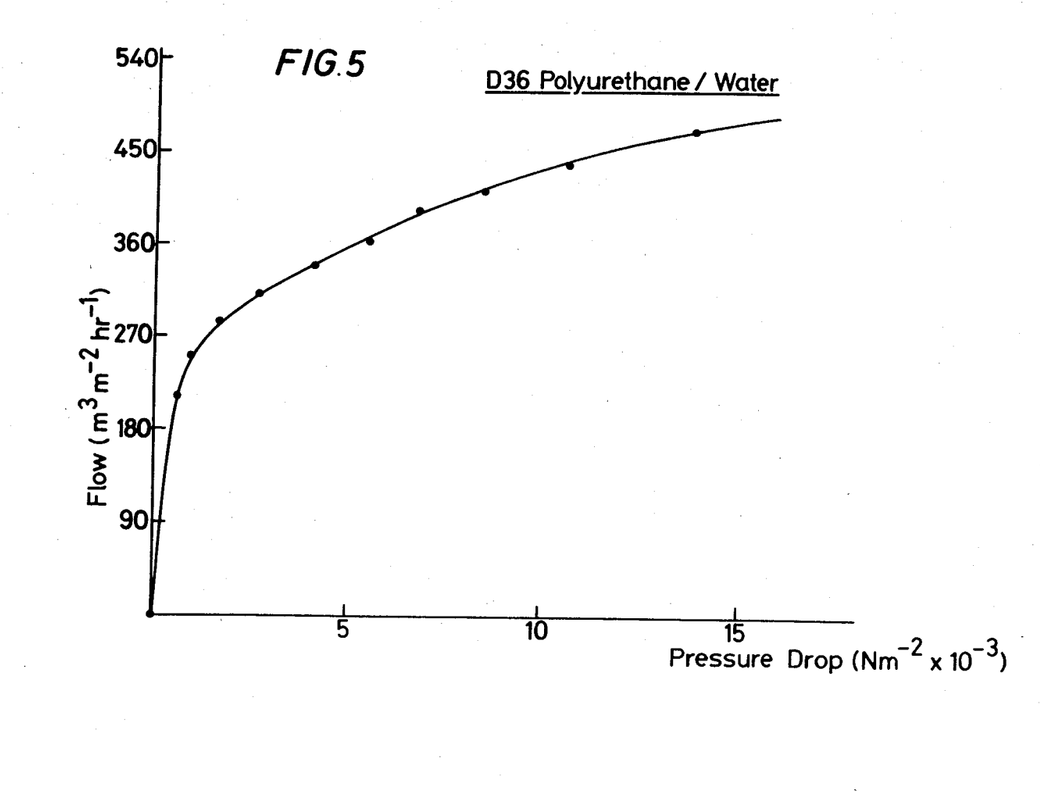

In the results of Tables 4 and 5 which are shown graphically in FIGS. 4 and 5, the altered resistence to flow of the deformed matrices is indicated by the relationship between pressure drop and liquid flow rate across the foam, when a steady-state deformation of the matrix had been established.

TABLE 4

(c) Polyurethane D7

(i) Glucose syrup flowing at 25° C.    Viscostiy = 6400 cP

| Flow ($m^3 m^{-2} hr^{-1}$) | Pressure drop ($Nm^{-2} \times 10^{-3}$) |
|---|---|
| 0.11 | 2.40 |
| 0.15 | 7.07 |
| 0.20 | 11.3 |
| 0.30 | 22.7 |
| 0.33 | 27.8 |

(ii) Glucose syrup flowing at 15° C.    Viscosity = 17500 cP

| Flow ($m^3 m^{-2} hr^{-1}$) | Pressure drop ($Nm^{-2} \times 10^{-3}$) |
|---|---|
| 0.06 | 7.07 |
| 0.08 | 17.1 |
| 0.085 | 22.7 |
| 0.10 | 25.3 |
| 0.11 | 27.6 |

TABLE 5

(d) Polyurethane D36

Water flowing at 20° C.    Viscosity = 1 cP

| Flow ($m^3 m^{-2} hr^{-1}$) | Pressure drop ($Nm^{-2} \times 10^{-3}$) |
|---|---|
| 213 | 0.59 |
| 285 | 1.67 |
| 312 | 2.65 |
| 339 | 4.03 |
| 363 | 5.49 |
| 393 | 6.77 |
| 411 | 8.43 |
| 435 | 10.6 |
| 468 | 13.7 |

The following experiments illustrate that the change of compaction of a porous matrix as a function of flow rate depends on the nature of that matrix.

Figure 6:
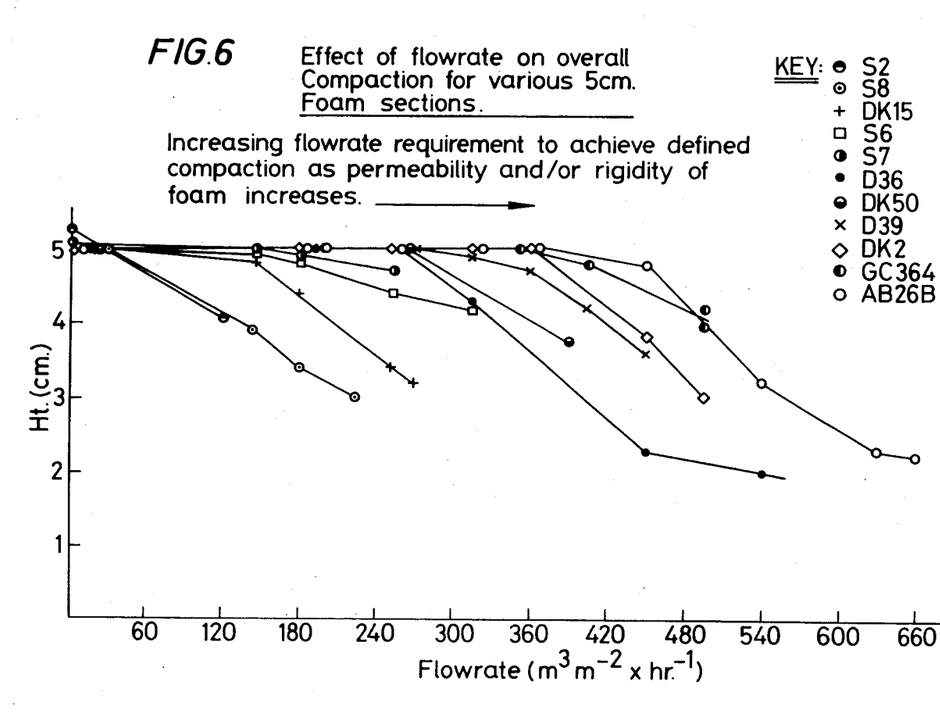
FIG. 6 shows a graph of the change of compaction of a number of porous matrices as a function of flow rate of water.
Figure 7:
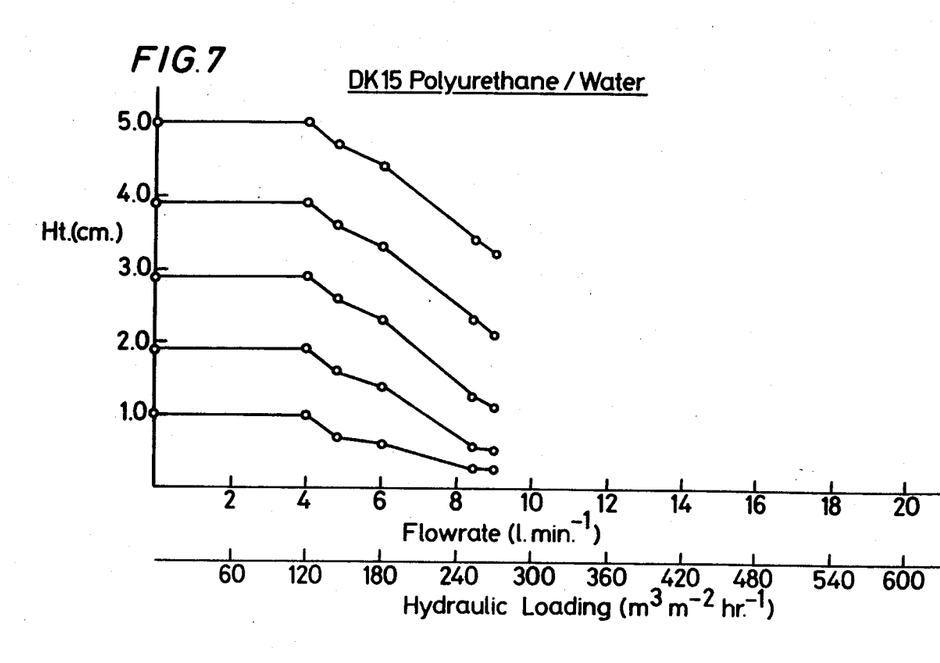
FIGS. 7 to 10 show graphs of the non-uniform deformation of various polyurethane foams, latex rubber foams and latex granules for various water flow rates.
Figure 8:
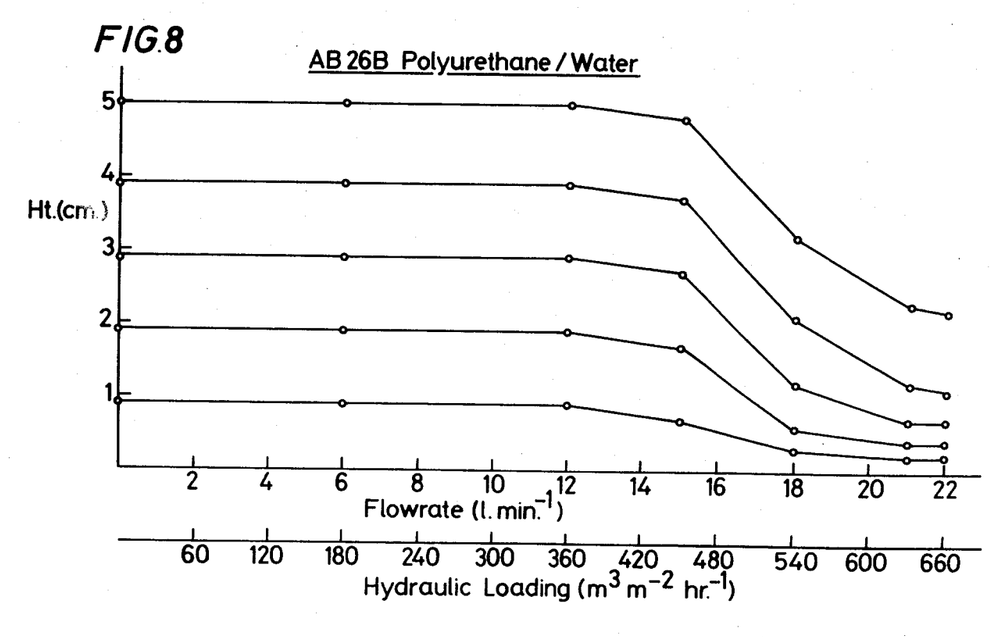
Figure 9:
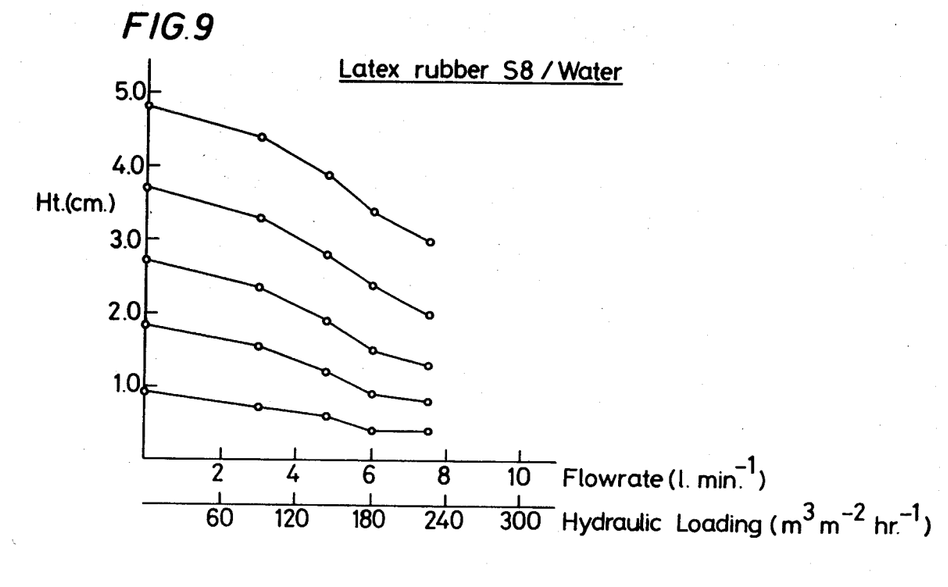
Figure 10:
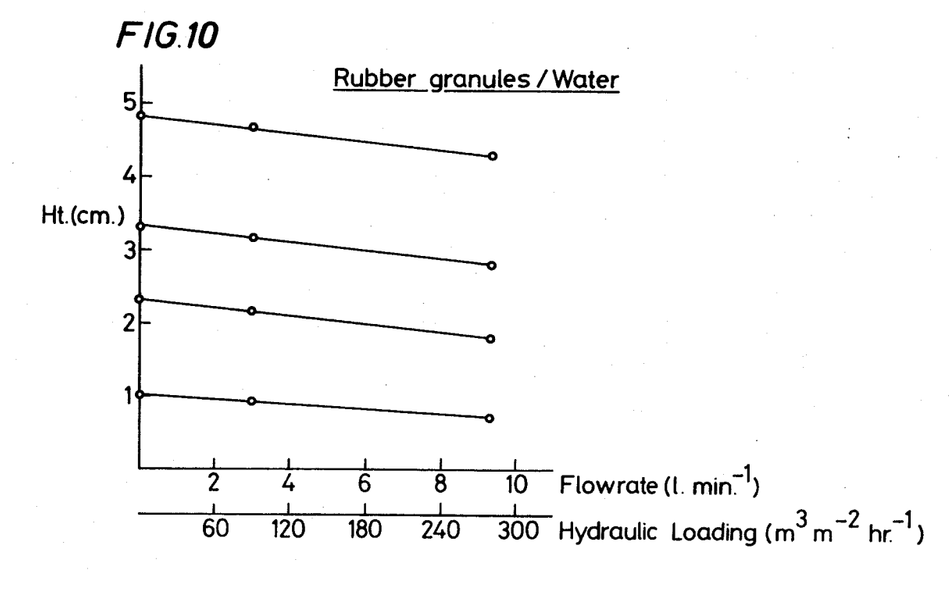

A number of matrices were cut into cylinders 5 cm in diameter and 5 cm in length. Each cylinder was inserted in turn into the flow tube 1 in which it was supported on a wire mesh grid. Water was passed vertically downwards through each matrix at a series of flow rates and the overall degree of compaction at each flow rate was measured. Compaction profiles are shown in FIG. 6. As can be seen for polyurethane foams the compaction of the matrix does not occur until higher fluid flow rates are reached. The degree of compaction depends on several factors e.g. the nominal undeformed pore size of the matrix. Thus as the pore size increases, the flow rate required to cause deformation increases or for a given flow rate greater compaction can be achieved with a smaller matrix pore size. Also compaction of the matrix is dependent on the rigidity of the matrix. Thus two foams of identical density and pore size may exhibit different compaction profiles if their inherent rigidity differs. The maximum compaction which can be achieved with a porous matrix appears to depend on the void space present. Thus the degree of compaction achieved on applying a static loading of 9.8N to a series of similar polyurethane foams varies inversely with foam density. This is shown in Table 6 below.

TABLE 6

| Foam | Density ($Kgm^{-3}$) | Overall Compaction |
|---|---|---|
| DK2 | 14 | 80% |
| DK15 | 30 | 70% |
| DK50 | 50 | 50% |

The term overall compaction is defined as [(ho-hf)/ho]×100% where ho is the undeformed matrix height and hf is the compacted matrix height. The foam was in the form of a 5 cm×5 cm cylinder.

Also for a single porous matrix, the degree of compaction at constant flow rate is dependent on the height of the porous matrix. Thus for the foamed polyurethane DK50, a decrease in the height of the undeformed matrix leads to a decrease in both the overall compaction and the percentage compaction at the restrained edge.

The following examples show that non-uniform compaction occurs not only with polyurethanes of varying properties but also with latex rubber foams and porous matrices consisting of discrete elastically deformable particles.

Five centimeter cylindrical sections of various porous matrices were marked with transverse reference lines 4 as shown in FIG. 1 and inserted into flow tube 1. (With the granular material it was necessary to dye alternate 1 cm sections to facilitate the observation of compaction within the matrix). Water was passed through each matrix at different flow rates and the degree of deformation along its length was measured by referring to the graduation points. Non-uniform deformation is shown in FIGS. 7 to 10.

The flow rate and pressure drop across the porous matrix at which non-uniform deformation occurs is matrix dependent and dependent upon the degree of material entrapment. Conventional filter media tend to be operated at flow rates of water of less than 50 cubic meters/sq. meter/hour. The flow rate for the onset of appreciable non-uniform deformation of a porous matrix may be as little as 90 or as large as 540 cubic meters/sq. meter/hour or more, dependent upon pore size, matrix thickness, and the degree of solids entrapment.

Figure 11:
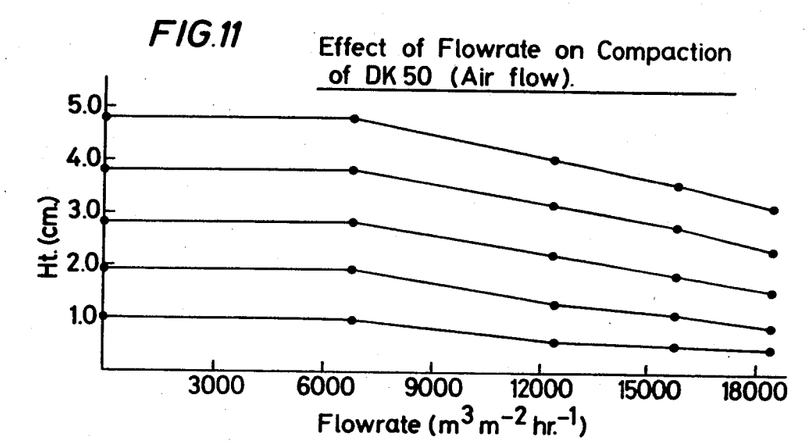
FIG. 11 shows a graph of the non-uniform deformation of DK50 in response to air flow.

FIG. 11 shows that non-uniform deformation can also be achieved when using air (viscosity $1.8 \times 10^{-2}$ cP) as the continuous fluid phase. Relatively high flow rates ($\sim 10{,}000$ m$^3$m$^{-2}$hr$^{-1}$) are required to achieve appreciable compaction in this case.

The following experiment relates to the separation of particles within a porous matrix according to size.

A 5 cm long cylindrical section of D36 polyurethane foam was sliced transversely into five 1 cm sections [numbered 1 (upstream section)-5 (downstream section)] and inserted into the flow tube 1 (FIG. 1). Water was flowed through the matrix at an initial rate of 510 m$^3$m$^{-2}$h$^{-1}$ and pressure drop of $9.86 \times 10^3$ Nm$^{-2}$ resulting in non-uniform compaction from 5 cm to 2.4 cm (53% compaction). About 4 g of silica particles having particle sizes in the range 63 to 200 μm were injected into the water flow over a period of about ¼ hour. During this time the flow fell to 90 m$^3$m$^{-2}$h$^{-1}$ and the pressure drop (ΔP) across the matrix increased from 9.86 to $22.76 \times 10^3$ Nm$^{-2}$ the matrix further compacting from 2.4 to 2.0 (60% compaction). The water flow was then stopped. Each section of foam was carefully removed from the system and squeezed repeatedly to release trapped particles. Analysis of the particles from each individual section by Coulter Counter indicated that the coarser particles tended to be retained at the upstream part of the matrix while the finer particles tended to be retained at the downstream part. Weight determination of the solids from each section indicated that most of the material was being removed by Sections 1 and 2. Results are summarised in Table 7.

TABLE 7

| Porous Matrix | Section No. | Flow Rate Initial m$^3$m$^{-2}$hr$^{-1}$ | Flow Rate Final m$^3$m$^{-2}$hr$^{-1}$ | ΔP (Nm$^{-2}$ × 10$^{-3}$) | Mean Particle Size (μm) | Percentage of Total Solids Retained |
|---|---|---|---|---|---|---|
| D36 Polyurethane | 1 | 510 | 90 | 9.86 22.76 | 143 | 36.3 |
| | 2 | | | | 117 | 42.0 |
| | 3 | | | | 87 | 11.1 |
| | 4 | | | | 78 | 6.4 |
| | 5 | | | | 72 | 4.2 |

A similar experiment, using the same foam matrix, but a different particle size range (15 to 40μ) resulted in similar overall findings. However the particles, being smaller, were mostly retained in sections 4 and 5.

The self cleaning ability of the present system has been demonstrated with several foam matrices. After the separation process has occurred, rapid variation of the fluid flow rate facilitates release of the entrapped solid particles. The extent of solids release appears to depend on the pore size of the matrix and the relative particle size. To obtain full relaxation of the downstream end of the porous matrix during solids release, gentle backwashing of the matrix may be used. Some results are shown in Table 8.

TABLE 8

| Porous Matrix | Recovery of Solids in situ (% weight) |
|---|---|
| Latex foam No. 8 | 40% |
| P/u foam No. DK50 | 67% |
| Latex foam No. 2 | 47% |

The following experiments show that as the fluid flow through a deformable matrix is increased i.e. as the compaction increases, the nominal pore size is decreased and hence filtration efficiency of the matrix is increased.

5 cm sections of various matrices were inserted in turn into flow tube 1. Water, containing suspended silica particles, was passed through the matrix at a sufficiently low flow rate not to induce deformation. The ability of the matrix to remove the solid material from the water (Filtration Efficiency) was determined by counting the number of particles in samples taken both upstream and downstream of the matrix. Particle counting was performed by Coulter counter and filtration efficiency (%) was defined as:

$$\frac{\text{Number of particles in upstream sample} - \text{number of particles in downstream sample}}{\text{Number of particles in upstream sample}} \times 100\%$$

Flow rate through the matrix was then increased to induce nonuniform compaction and its filtration efficiency was again calculated. Results shown in Table 9 confirm that increasing flow rate through the matrix improves its filtration performance. This is in contrast to conventional filtration techniques involving an undeformed porous matrix where in general the greater the flow rate the poorer the filtration efficiency.

The following experiments describe the separation of particles and their subsequent release, in this case Sephadex (a dextran polymer manufactured by Pharmacia A/B) particles from a liquid other than water, in this case, glucose syrup.

Sephadex particles with diameters in the range 30-150 μm were suspended in glucose syrup. The matrix of D7 polyurethane was nonuniformly deformed by flowing through it glucose syrup at 25° C. The flow rate was 0.33 m$^3$m$^{-2}$hr$^{-1}$ and the pressure drop was $27.8 \times 10^3$ Nm$^{-2}$. A bolus of the suspended particles was introduced into the liquid flowing into the foam matrix and aliquots were sampled at the outflow. The mean diameter of the particles introduced was 63 μm. The mean diameter of the particles collected from the outlet of the deformed foam was 45 μm. A distinct band of trapped Sephadex particles was visible in the matrix just above the level where deformation was maximal. When no further particles were observable in the liquid outflow, flow was then halted and the matrix spontaneously expanded. Flow was then restarted at approximately 0.07 m$^3$m$^{-2}$hr$^{-1}$. Particles then reappeared in the outflow, their concentration being eight times greater than that observed as the bolus emerged from the deformed matrix. Their mean diameter was 67 μm.

The following experiment demonstrates how the accumulation of solids within a deformable matrix may alter its compaction characteristics in response to flow.

Figure 12:
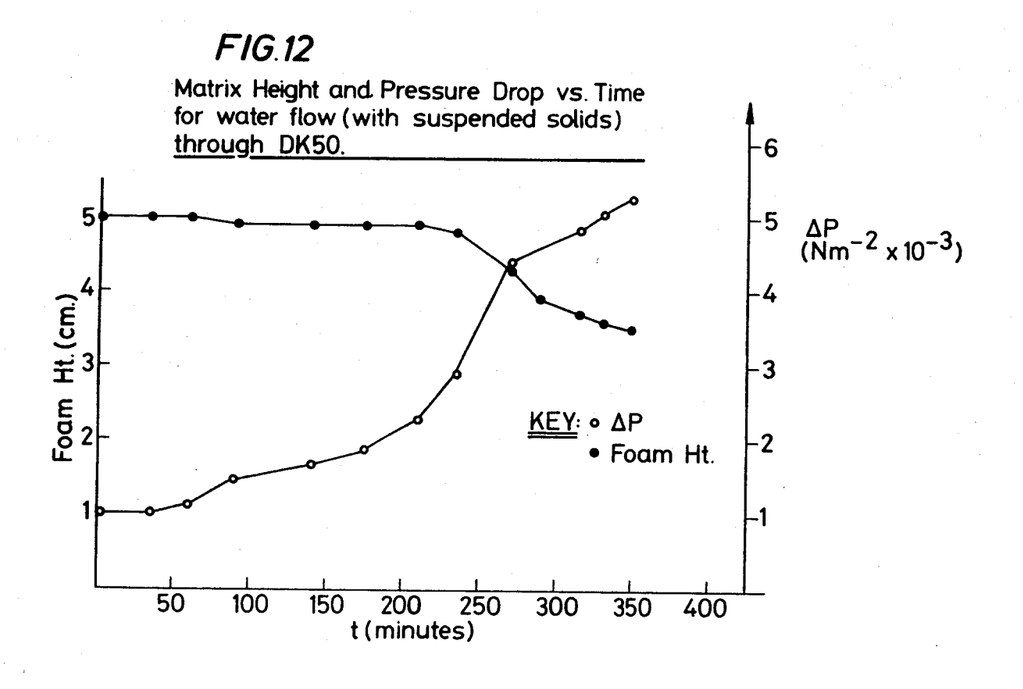
FIG. 12 shows a graph of the deformation of DK50 in response to solids deposition within the matrix.

Water containing suspended silica particles (23 mgl$^{-1}$) was passed through a 5 cm long cylindrical section of DK50 polyurethane foam at a flow rate of 90 m$^3$m$^{-2}$h$^{-1}$. This was insufficient to cause compaction. However after continuous operation for about 1 to 2 hours, accumulation of solids within the matrix caused the onset of deformation. Non-uniform deformation continued to increase as more solid material was deposited. This phenomenon, which is shown in FIG. 12, may be used to alter the retention characteristics of a matrix by the deliberate addition of chosen particles.

TABLE 9

| Matrix | State of Matrix | Matrix Height (cm) | Flow Rate $m^3m^{-2}hr^{-1}$ | Particle Concentration $mg\ l^{-1}$ | Filtration Efficiency (%) |
|---|---|---|---|---|---|
| D36 | Relaxed | 5.0 | 90 | 18 | 6.7% (>10μ)<br>12.5% (>10μ) |
| D36 | Compacted | 2.5 | 420 | 18 | 13% (>10μ)<br>16.2% (>13μ)<br>21.4% (>16μ)<br>28.3% (>20μ) |
| DK50 | Relaxed | 5.0 | 90 | 23 | 3.9% (>10μ)<br>5.3% (>13μ)<br>8.2% (>16μ)<br>14.3% (>20μ) |
| DK50 | Compacted | 3.5 | 285 | 23 | 29.1% (>10μ)<br>33.1% (>13μ)<br>37.6% (>16μ)<br>46.1% (>20μ) |
| C | Relaxed | 4.8 | 90 | 38 | 0% (>10μ)<br>1.5% (>16μ)<br>3.4% (>20μ) |
| C | Compacted | 4.3 | 300 | 38 | 13.2% (>10μ)<br>15.8% (>16μ)<br>19.8% (>16μ)<br>25.2% (>20μ) |
| S2 | Relaxed | 5.0 | 45 | 40 | 1.8% (>10μ)<br>1.6% (>13μ)<br>3.1% (>16μ)<br>11.3% (>20μ) |
| S2 | Compacted | 4.0 | 90 | 40 | 21.0% (>10μ)<br>21.9% (>13μ)<br>26.8% (>16μ)<br>43.5% (>20μ) |

(Particles being monitored were silica having diameters of 10 to 25 μm)

I claim:

1. A process for separating suspended material from a fluid comprising
    (i) steadily flowing a fluid containing suspended material through a porous matrix closely fitting within a flow line, the porous matrix being restrained at either the fluid inlet or the fluid outlet face
    (ii) the porous matrix being fabricated from a material capable of elastic deformation and containing material which is chemically reactive with the suspended material
    (iii) the fluid flow rate being sufficiently large so as to produce substantial non-uniform drag-induced deformation of the porous matrix, the deformation thereby creating a gradient of porosity in the porous matrix in the direction of fluid flow and
    (iv) the gradient of porosity enabling the separation of at least a part of the suspended material within the porous matrix.

2. A process for separating suspended material from a fluid comprising
    (i) steadily flowing a fluid containing suspended material through a porous matrix closely fitting within a flow line the average pore size of the undeformed porous matrix being greater than the average particle size of the suspended material, the porous matrix being restrained at either the fluid inlet or the fluid outlet face
    (ii) the porous matrix being fabricated from a material capable of elastic deformation
    (iii) the fluid flow rate being sufficiently large so as to produce substantial non-uniform drag-induced deformation of the porous matrix, the deformation thereby creating a gradient of porosity in the porous matrix in the direction of the fluid flow and
    (iv) the gradient of porosity enabling the separation of at least a part of the suspended material within the porous matrix.

3. A process according to claim 1 or 2 in which the fluid flow rate through the porous matrix is 90 $m^3m^{-2}hr^{-1}$ or more and the deformation of the porous matrix is 10% or more for fluids having a viscosity of 5 cp or less at the temperature of the separation process.

4. A process according to claim 1 or 2 in which the porous matrix is restrained by means of a substantially non-deformable member at the outlet side of the porous matrix.

5. A process according to claim 1 or 2 in which the whole or part of the suspended material is released from the porous matrix in the direction of fluid flow by reducing the fluid flow rate.

6. A process according to claim 1 or 2 the whole or part of the suspended material is released in the direction of fluid flow from the porous matrix by rapidly varying the fluid flow rate between zero and an operating flow rate.

7. A process according to claim 1 or 2 in which a solid particulate material of varying particle size suspended in the fluid is flowed through the porous matrix for a time sufficient to cause fractionation of the solid particulate material according to particle size within the porous matrix.

8. A process according to claim 7 in which the fractions of particulate material are removed from the porous matrix by a physical procedure.

9. A process according to claim 1 or 2 in which the porous matrix is in the form of a cylinder having a fluid inlet face and a fluid outlet face.

10. A process according to claim 1 or 2 in which the porous matrix is in the form of an annular cylinder, the fluid flow being from the inside of the cylinder to the outside or vice-versa.

11. A process according to claim 1 or 2 in which the fluid is a liquid or gas.

12. A process according to claim 11 in which the liquid is water based.

13. A process according to claim 11 in which the liquid is in the form of an emulsion.

14. A process according to claim 13 in which the emulsion is an oil/water emulsion.

15. A process according to claim 1 or 2 in which the porous matrix is a foamed plastics material, discrete elastically deformable particles or an elastically deformable felt material.

16. A process according to claim 15 in which the foamed plastics material is a polyurethane foam or a rubber based foam.

17. A process according to claim 1 or 2 in which the retained material is removed from the porous matrix by backwashing.

* * * * *